United States Patent [19]

Kamaya

[11] Patent Number: 5,623,951
[45] Date of Patent: Apr. 29, 1997

[54] WRIST EXTENDING BOARD FOR CANNULATION OF A CATHETER AND/OR ARTERIAL BLOOD SAMPLING AND METHODS FOR USING SAME

[76] Inventor: Hiroshi Kamaya, 3710 E. Eastwood Dr., Salt Lake City, Utah 84109

[21] Appl. No.: 643,312

[22] Filed: May 10, 1996

[51] Int. Cl.$^6$ ..................................................... A61F 5/37
[52] U.S. Cl. ........................... 128/877; 128/878; 602/21
[58] Field of Search .................................. 128/869, 877, 128/878, 879, DIG. 26; 2/16, 910, 161.1; 5/601, 623, 646, 647; 602/5, 20, 21, 22

[56] References Cited

U.S. PATENT DOCUMENTS

| | | | |
|---|---|---|---|
| 1,797,057 | 3/1931 | Foulke | 602/21 |
| 3,074,399 | 1/1963 | Bitting | 128/879 |
| 3,901,227 | 8/1975 | Klatskin | 128/133 |
| 4,011,596 | 3/1977 | Chang | 2/16 |
| 4,369,774 | 1/1983 | Robbins | 128/133 |
| 4,502,477 | 3/1985 | Lewis | 128/133 |
| 4,928,712 | 5/1990 | Mele | 128/877 |
| 4,982,744 | 1/1991 | Stanec | 128/877 |
| 5,083,575 | 1/1992 | Jones | 128/877 |
| 5,136,743 | 8/1992 | Pirela-Cruz | 128/878 |
| 5,327,912 | 7/1994 | Mally | 5/647 |

OTHER PUBLICATIONS

Advertisement literature for Patient Restraining Aids, Winter/Spring, 1994, p. 74, distributed by Gary Hull Anesthesia, Inc., Huntington Beach, Calif.

Primary Examiner—Michael A. Brown
Attorney, Agent, or Firm—Broadbent, Hulse, Pierce & Pate

[57] ABSTRACT

A wrist extending board for cannulation of a catheter and/or arterial blood sampling is disclosed as including an elongated cannulation board having a first end, a second opposing end and several angular bends disposed therebetween. In preferred design, the longitudinal configuration of the cannulation board provides a contoured shape forming an angle of extension sufficient for hyperflexing the supinated hand and wrist of a patient to sufficiently expose the volar aspect of the wrist for cannulation or arterial blood sampling by way of penetrating the radial artery. Preferably disposed approximate the second end of the cannulation board is a fixation member forming an open cavity. The cavity provides an opening for introducing a substantial portion of the supinated hand of the patient therein and further provides means for securing the hand, wrist and forearm of the patient in a fixed relationship with the cannulation board. In addition, at least one retaining member may be formed contiguous with the second end of the cannulation board to provide means for engageably retaining an arterial cannula and its attached tubing for ready access after cannulation or blood sampling.

20 Claims, 4 Drawing Sheets

WRIST EXTENDING BOARD FOR CANNULATION OF A CATHETER AND/OR ARTERIAL BLOOD SAMPLING AND METHODS FOR USING SAME

BACKGROUND

1. The Field of the Invention

This invention relates to cannulation boards and, more particularly, to novel systems and methods for maintaining the wrist of a patient in an extended position for cannulation of a catheter and/or arterial blood sampling.

2. The Background Art

Invasive hemodynamic monitoring of cardiovascular function has become an integral and virtually routine aspect of intensive care units and operating rooms. One of the greatest values of hemodynamic monitoring is that it usually provides an improved understanding of the pathophysiology of the patient's current disorder and, in turn, often facilitates the making of a specific diagnosis. For this purpose, the information collected by means of hemodynamic monitoring may be used to guide the choice of initial therapy. After therapy is started, hemodynamic monitoring may be used to measure systemic blood pressure and direct transduction of the pressure waveform, whereby providing means for alerting caregivers as to physiological changes in the status of the patient and the effect of therapeutic intervention. Moreover, the measurements obtained by way of hemodynamic monitoring are typically useful in predicting prognosis.

Traditionally, invasive hemodynamic monitoring includes direct measurement of either the arterial pressure by means of an arterial cannula, central venous pressure by means of a central venous catheter, intracardiac pressures and flows by means of a pulmonary artery catheter, or by some combination of the three. The indications for using each of the foregoing modalities for invasive monitoring of cardiac status are usually determined by balancing the likelihood of obtaining useful information from a specific hemodynamic monitoring technique against the inherent risks and/or discomfort of the technique as realized by the patient.

Arterial pressure monitoring by means of an indwelling, peripheral arterial catheter is one of the most commonly used techniques of invasive hemodynamic monitoring. The general benefits of arterial pressure monitoring are: (1) continuous, precise, reproducible measurements of systolic, diastolic, and mean blood pressure; (2) accurate diagnosis of hemodynamic disorders characterized by fluctuations in blood pressure; (3) guidance in the choice of therapy for hypotension or hypertension; (4) continuous monitoring of the effect of therapy, allowing frequent adjustment of therapy for hypotension or hypertension; and (5) monitoring the patient's response to drug therapy. Another important benefit of an indwelling, peripheral arterial cannula is that it allows painless blood drawing from patients who would otherwise require multiple arterial and/or venous punctures for blood sampling. Incidently, an indwelling arterial catheter can add considerably to the comfort of such a patient by avoiding the pain and local injury associated with frequent arterial and/or venous punctures. In this regard, an arterial cannula may be placed more to optimize patient comfort than to monitor arterial blood pressure.

As readily appreciated by those skilled in the art, invasive arterial cannulation may be performed, for example, at the radial, ulnar, brachial, femoral, dorsalis pedis and axillary arteries. The radial artery is usually selected as the site for the placement of a peripheral arterial catheter due to its accessibility and the generally good collateral circulation supplied by the ulnar artery. Similarly, the radial artery is a good site for obtaining an arterial blood sample because it is superficially located and relatively easy to palpate and stabilize, is not adjacent to large veins and a probing needle should be relatively pain free as long as the periosteum of surrounding bone is avoided. Cannulation of the radial artery also seems to cause the least discomfort for patients since it allows considerable freedom of movement and typically does not require the immobilization of the joint. Further, the risk of ischemic injury to the hand and digits associated with radial artery catheterization is presumably low due to the presence of ample collateral circulation between the radial and ulnar arteries.

Although invasive, peripheral arterial cannulation can be performed reasonably safely in clinical settings, there is some risk of local infection, arterial occlusion and embolization. Consequently, cannulation is typically performed by personnel trained in such techniques or procedures. As appreciated by those skilled in the art, cannulation of a catheter in the radial artery or drawing an arterial blood sample from the radial artery at the wrist generally requires a patient's cooperation to extend the wrist during the cannulation procedure. This may require the aide of an assistant to maintain the wrist of the patient in an extended supine position or, in the alternative, the application of a means for hyperflexing the wrist of the patient in order to support an angle of extension whereby adequately exposing the radial artery for palpating and cannulation.

In accordance with one such prior art technique or method for cannulating a catheter in the radial artery, the wrist of a patient may be extended in a supine position by placing a towel or pillow under the wrist. In this manner, prior art radial cannulation methods generally provide a means for securing the wrist in relation to the towel or pillow by way of wrapping an adhesive tape around the towel or pillow and then around the hand, wrist and forearm of the patient one or more times to sustain a fixed relationship therebetween.

A significant disadvantage with prior art cannulation methods utilizing a towel or pillow to support the wrist of a patient in a supinated position readily embraces complications realized in attempting to support the wrist in an angle of extension suitable for adequately exposing the artery of the patient for cannulation or blood sampling. Moreover, prior art cannulation armboards or methods using adhesive tape to secure the hand, wrist and forearm of the patient to an armboard or cushioning means necessitates the removal of the portion of tape contacting the skin of the hand, wrist and forearm which inherently results in significant discomfort and probable pain upon its removal.

As technology progressed, prior art cannulation boards were developed by those skilled in the art comprising a cavity formed in the bottom of a flat, rigid armboard wherein a portion of the hand of a patient may be placed and a contoured wedge piece may be removably positioned adjacent the wrist joint to provide support for thrusting the wrist upward into an extended position. A serious disadvantage with prior art cannulation boards of this type is the general discomfort felt by the patient in relation to forcibly displacing the wrist joint into a hyperflexed position by means of a small rigid, contoured wedge piece.

To avoid the foregoing disadvantages in relation to the identifiable pain associated with removing adhesive tape from the skin of a patient and the inherent discomfort of forcibly thrusting a wrist joint upward into a hyperextended position, various other embodiments of cannulation boards were conceived by those skilled in the art in an attempt to alleviate the foregoing intrusions. For example, prior art cannulation boards were developed comprising multiple belts, straps, hook and loop fasteners, modified hook and loop fasteners or other conventional fastening means for retaining the hand, wrist and forearm of a patient in fixed relation to the cannulation board. One of such prior art cannulation boards consists of a flat, rectangular board having an upper surface including a fabric hook fastener removably interlocking with a fabric loop fastener formed on the bottom surface of a composite sheet. Disposed on the upper surface of the composite sheet is an adhesive covering which provides a means for rigidly securing the hand, wrist and forearm of the patient in relation thereto, thus becoming a single unit which can be easily removed and reattached to different armboards in various locations in a hospital, such as, for example, an operating room, recovery room, intensive care unit, etc.

A significant disadvantage to cannulation boards as disclosed above is their inability to provide a means for easily mounting or dismounting the hand, wrist and forearm from the cannulation board without having to manually release several restraining bands or straps or, in the alternative, without having to remove adhesive tape wrapping or an adhesive composite sheet from the skin of the patient's hand, wrist and forearm. In addition, prior art cannulation boards comprising multiple bands or straps are usually more difficult to clean and sterilize in view of the active bleeding that typically takes place from the site of needle penetration. For this reason, prior cannulation boards are generally discarded after initial utilization because of the potential contamination and, more especially, in view of passing infectious diseases to another patient. As will be further appreciated by those skilled in this particular art, economic considerations are significant when dealing with the highly competitive medical industry, since relatively complicated cannulation armboards comprising multiple working components (e.g., belts, straps, hook and loop fasteners, etc.) are frequently found to be commercially impractical. In this regard, even a slight savings in cost by way of reducing the number of working parts may substantially increase or enhance the commercial appeal of a particular cannulation board when considering relevant issues of its application or mass production.

Although prior art cannulation boards generally afford meaningful advantages over the use of towels or pillows, the overall effectiveness of such prior art cannulation boards has been frequently questioned in view of providing adequate and efficient means by which to expose the volar aspect of the wrist while preventing rotation of the hand, wrist and arm from its artificially supinated position in relation to the natural force acting on the hand, wrist and arm to pronate or rotate back into its neutral position.

Consistent with the foregoing and as illustrated by the number of prior art patents and other disclosures, efforts are continuously being made in an attempt to remedy the above-identified disadvantages. While prior art cannulation boards may appear generally suitable for their intended purpose, they nevertheless leave much to be desired from the standpoint of simplicity of construction, effectiveness of operation, functionality as to universal application and overall manufacturing costs. In this regard, the present invention provides for a novel wrist extending cannulation board and methods which overcome several deficiencies of cannulation boards of the prior art and resolves several problems left unsolved by known prior art.

BRIEF SUMMARY AND OBJECTS OF THE INVENTION

In view of the foregoing, it is a primary object of the present invention to provide a novel wrist extending board having a contour shape providing an angle of extension sufficient for hyperflexing the wrist of a patient while adequately exposing the volar aspect of the wrist for cannulation of a catheter and/or arterial blood sampling.

It is also an object of the present invention to provide a wrist extending board for cannulation of a catheter and/or arterial blood sampling and methods for using same which provides a means for easily mounting or dismounting the hand, wrist and forearm of a patient.

Further, it is an object of the present invention to provide a wrist extending board for cannulation of a catheter and/or arterial blood sampling which comprises a novel fixation member providing means for securing the hand of the patient in a supinated position, without the need for multiple working components, while further preventing pronation of the hand, wrist and forearm into its neutral position in relation to the natural rotational forces acting thereagainst.

It is a still further object of the present invention to provide a wrist extending board for cannulation of a catheter and/or arterial blood sampling which is capable of being readily cleaned and sterilized for immediate reuse by another patient.

Similarly, it is an object of the present invention to provide a wrist extending board for cannulation of a catheter and/or arterial blood sampling which provides a means for mounting the arterial tubing for easy availability in relation to reducing blood loss after the cannulation procedure.

Additionally, it is an object of the present invention to provide a wrist extending board for cannulation of a catheter and/or arterial blood sampling which is capable of being adaptable for pre-sterilization and for packaging as a disposable product, thus being generally cost effective in light of mass production and readily available for emergency procedures.

It is likewise an object of the present invention to provide a wrist extending board for cannulation of a catheter and/or arterial blood sampling which comprises hingeable connections for making the board compact for portability.

Consistent with the foregoing objects, and in accordance with the invention as embodied and broadly described herein, a wrist extending apparatus is disclosed in one presently preferred embodiment of the present invention as including an elongated cannulation board having a first end, a second opposing end and several angular bends disposed therebetween. In preferred design, the longitudinal configuration of the cannulation board provides a contoured shape forming an angle of extension sufficient for hyperflexing the supinated hand and wrist of a patient to sufficiently expose the volar aspect of the wrist for cannulation or arterial blood sampling by way of penetrating the radial artery. Preferably disposed approximate the second end of the cannulation board is a fixation member forming an open cavity. The cavity provides an opening for introducing a substantial portion of the supinated hand of the patient therein and further provides means for securing the hand, wrist and forearm of the patient in a fixed relationship with the cannulation board. In addition, at least one retaining member may be formed contiguous with the second end of the cannulation board to provide means for retaining an arterial cannula and its attached tubing for ready access after cannulation or blood sampling.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

It will be readily understood that the components of the present invention, as generally described and illustrated in the Figures herein, could be arranged and designed in a wide variety of different configurations. Thus, the following more detailed description of the embodiments of the system and method of the present invention, as represented in FIGS. 1 through 4, is not intended to limit the scope of the invention, as claimed, but it is merely representative of the presently preferred embodiments of the invention.

The presently preferred embodiments of the invention will be best understood by reference to the drawings, wherein like parts are designated by like numerals throughout.

Figure 1:
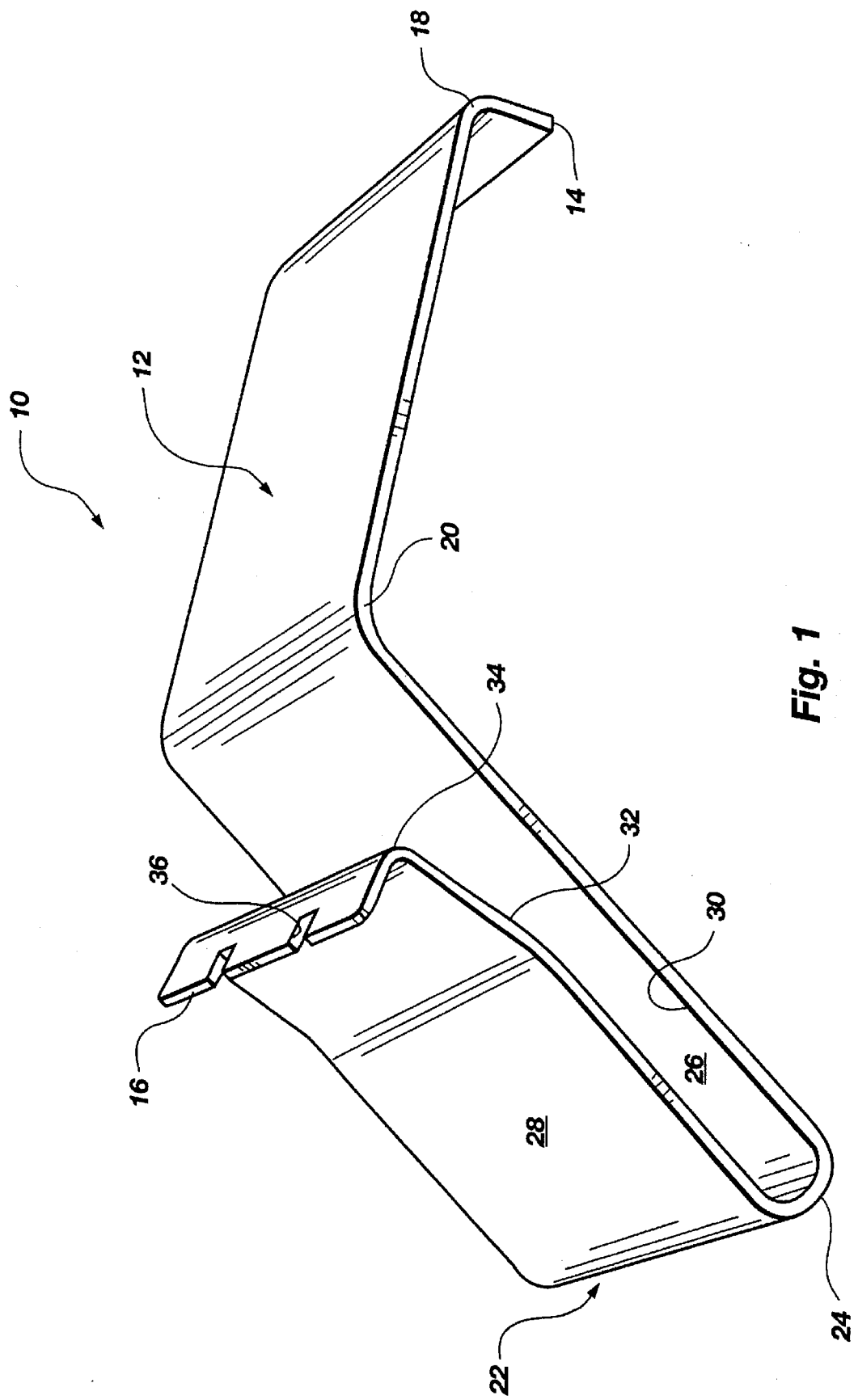
FIG. 1 is a perspective view of one presently preferred embodiment of the wrist extending board of the present invention.
Figure 2:
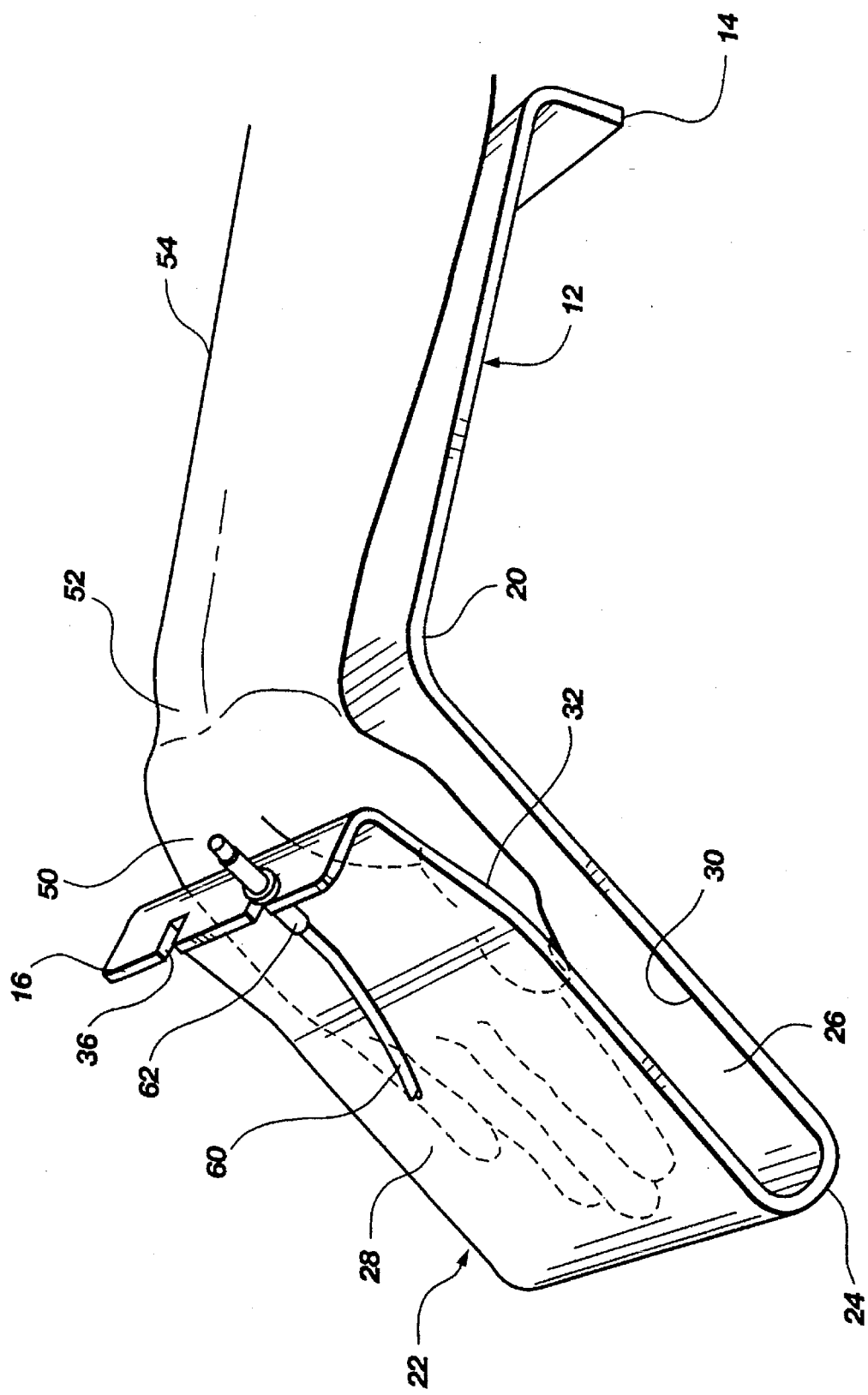
FIG. 2 is a perspective view of the embodiment of FIG. 1 illustrating the immobilization of a patient's hand according to the present invention.

One presently preferred embodiment of the wrist extending board for cannulation of a catheter and/or arterial blood sampling of the present invention, designated generally at 10, is illustrated in FIG. 1. As shown, the wrist extending board 10 comprises an elongated cannulation board 12 having a first end 14, a second opposing end 16 and several angular bends 18, 20, 24, 34 disposed therebetween. In preferred design, the longitudinal configuration of the cannulation board 12 provides a contoured shape forming an angle of extension sufficient for hyperflexing the supinated hand 50 and wrist 52 of a patient to sufficiently expose the volar aspect of the wrist 52 for cannulation or arterial blood sampling by way of penetrating the radial artery, as best shown in FIG. 2. Preferably disposed approximate the second end 16 of the cannulation board 12 is a fixation member 22. In structural operation, the fixation member 22 comprises a cavity 30. The cavity 30 provides an opening for introducing a substantial portion of the supinated hand 50 of a patient therein and further provides means for securing the hand 50, wrist 52 and forearm 54 of the patient in a fixed relationship with the cannulation board 12. In addition, at least one retaining member 36 may be formed contiguous the second end 16 of the cannulation board 12 to provide means for engageably retaining an arterial cannula 62 and its attached tubing 62 for ready access after cannulation or blood sampling. In preferred construction, the wrist extending board 10 is preferably formed of a rigid material being sufficiently sturdy to withstand stress or force without permanent or serious deformation and having a somewhat uniform thickness. In one presently preferred embodiment, the wrist extending board 10 of the present invention is formed of any of numerous organic, synthetic or processed materials that are mostly thermoplastic or thermosetting polymers of high molecular weight with or without additives, such as plasticizers, auto oxidants, colorants, or fillers, which can be shaped, molded, cast, extruded, drawn, foamed or laminated. It will be readily appreciated, however, that other suitable materials are possible. For example, the wrist extending board 10 may be formed of a metal or alloy, fiberglass, wood, ceramic (of or relating to any product as earthen-ware, porcelain, brick, glass, vitreous enamels, etc.), graphite composite or any other suitable polymeric or composite material known in the art to be sufficiently rigid.

Preferably, the material comprising the wrist extending board 10 is capable of being cleaned and/or sterilized by means of chemical treatment or autoclaving, thus providing a readily reusable cannulation board. Moreover, for commercial practicalities and for purposes of mass production, the wrist extending board 10 of the present invention may formed of a suitable disposable material.

As illustrated in FIGS. 1 and 2, a presently preferred embodiment of the cannulation board 12 of the wrist extending board 10 is anatomically configured and preferably formed having an upper surface area being sufficient in width to adequately support the hand 50, wrist 52 and forearm 54 of a patient when hyperflexing the wrist 52 of the patient to facilitate cannulation of the radial or ulnar artery. The upper surface area of the cannulation board 12 further comprises a substantially smooth surface, which, as used herein, means that the surface is substantially free from roughness and projections. Similarly, the cannulation board 12 may be formed including a fabric cover or foam padding longitudinally disposed along the upper surface of the cannulation board 12 to encourage comfort in its utilization. Preferably, the fabric covering or foam padding is comprised of a disposable material which may be removably disposed over the longitudinal surface of the cannulation board. As will be further discussed in greater detail hereinafter, the width of the upper surface area of the cannulation board 12 and the structural configuration of the fixation member 22 provide means for preventing pronation of the hand 50, wrist 52 and forearm 54 of the patient into a neutral position by means of the natural rotational forces acting thereagainst.

Consistent with the contoured configuration of the wrist extending board 10 of the present invention, the cannulation board 12 may be formed having a longitudinal surface extending substantially upward from a first end 14 and continuing therefrom to form a first angular bend 18. In structural operation, the first end 14 of the cannulation board 12 provides a surface abutment against the underlying surface upon which the wrist extending board 10 rests. As shown, the first angular bend 18 may form an angular bend in the longitudinal surface of the cannulation board 12 of between approximately 35° and 45°. In relation to one presently preferred embodiment of the present invention, the longitudinal surface of the cannulation board 12 preferably extends substantially upward from the first end 14 thereof at a length of approximately 4 cm to 4.5 cm to the first angular bend 18 which preferably comprises an angular bend of about 40°.

From the first angular bend 18, the longitudinal surface of the cannulation board 12 preferably extends at a substantially consistent incline to a second angular bend 20. The portion of the cannulation board 12 extending between the first angular bend 18 and the second angular bend 20 comprises a length sufficient to adequately support a significant portion of the supinated forearm 54 of a patient operably disposed in relation therewith. In one presently preferred embodiment of the present invention, the longitudinal surface of the cannulation board 12 disposed between the first angular bend 18 and the second angular bend 20 includes a linear length of approximately 10 cm to 15 cm, and preferably about 13 cm. As will be readily appreciated, the first end 14 of the cannulation board 12 may comprise a substantially consistent incline extending from the first end 14 to the second angular bend 20, without requiring the first angular bend 18 in the longitudinal surface of the cannulation board 12.

Extending from the second angular bend 20 of the cannulation board 12, the longitudinal surface provides a substantially consistent declining slope which engages a third angular bend 24. Disposed between the first angular bend 18 and the third angular bend 24, the second angular bend 20 preferably provides an angular support apex sufficient for hyperflexing the supinated wrist 52 of a patient in order to expose the volar aspect of the wrist for cannulation of the radial or ulnar arteries and/or for arterial blood sampling. In this manner, the second angular bend 20 preferably comprises an angular bend between approximately 115° and 125°.

In accordance with one presently preferred embodiment of wrist extending board 10 of the present invention, the second angular bend 20 provides an angle of extension of about 120°. Additionally, the substantially declining slope formed in the longitudinal surface of the cannulation board 12 and disposed between the second angular bend 20 and the third angular bend 24 provides a length sufficient to adequately support the supinated hand 50 of a patient operably disposed in relation therewith. In preferred construction, the length of the longitudinal surface of the cannulation board 12 disposed between the second angular bend 20 and the third angular bend 24 is approximately 15 cm to 25 cm, and preferably about 20 cm.

Figure 3:
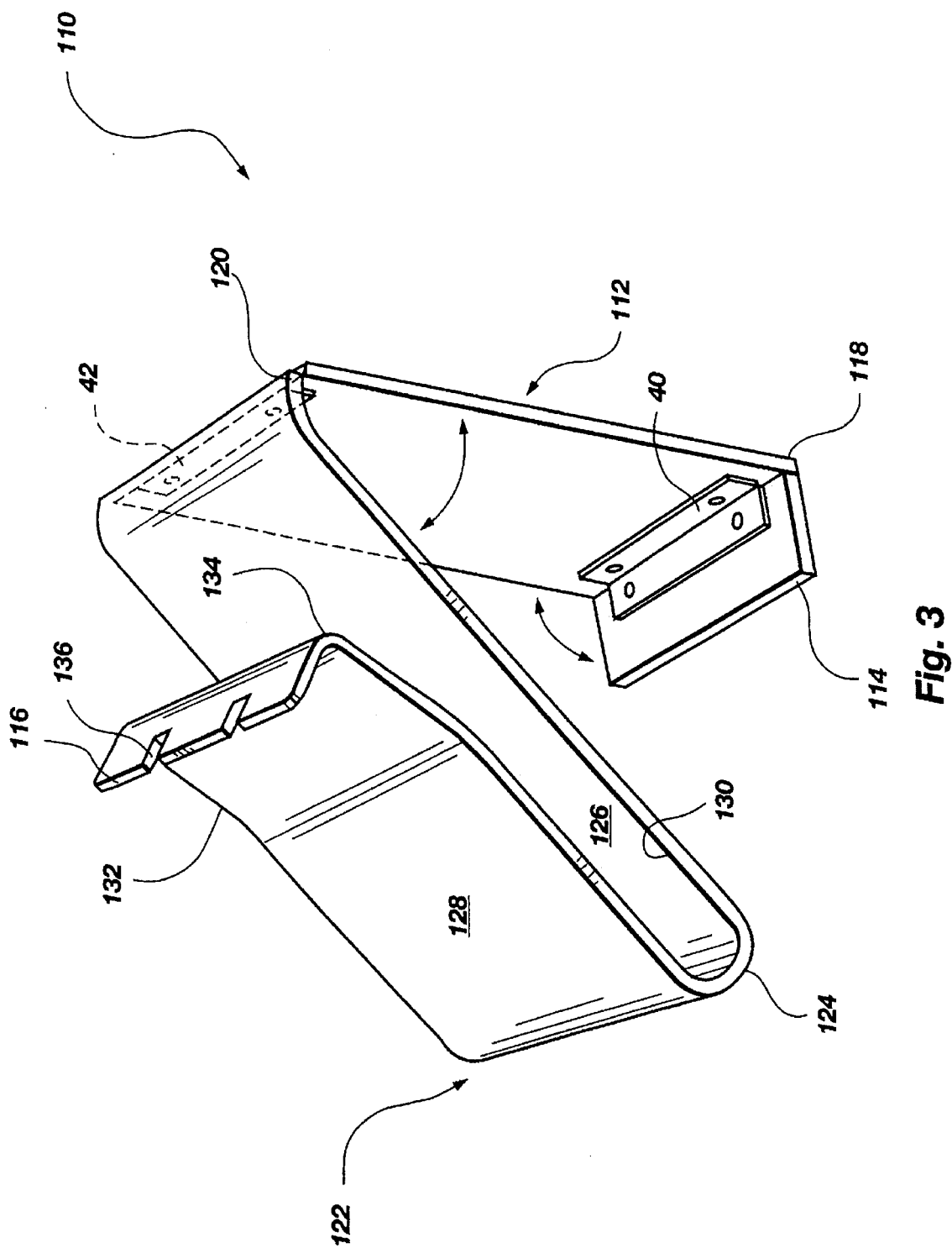
FIG. 3 is a front elevational view of an alternate preferred embodiment of the wrist extending board of FIGS. 1 and 2.

Referring now to FIGS. 1, 2 and 3, the third angular bend 24 disposed in the longitudinal surface of the cannulation board 12 is preferably formed having a substantially semicircular or U-shaped configuration. Consistent with the structural configuration of the third angular bend 24, a fixation member 22 is preferably formed having an upper portion 28 disposed in a spaced apart relationship to a lower portion 26 of the longitudinal surface of the cannulation board 12. In preferred design, the fixation member 22 provides a cavity 30 having an internal periphery substantially defined between the upper portion 28 of the fixation member 22 and the lower portion 26 of the cannulation board 12.

In one presently preferred embodiment of the fixation member 22, the cavity 30 consists of an opening having at least one peripheral side wall angularly defined by the U-shaped configuration of the third angular bend 24. As will be readily appreciated, however, the cavity 30 may be formed having one or more additional peripheral side walls disposed in such a manner as to provide for at least one opening wherein the fingers (including the thumb) and supinated hand 50 of the patient may be introduced.

Preferably, the internal periphery of the cavity 30 of the fixation member 22 provides a dimension sufficient in height to allow for the introduction of the fingers and the supinated hand 50 of a patient. In operation, the fingers (including the thumb) and a substantial portion of the palmer region of the supinated hand 50 of a patient may be disposed between the lower portion 26 of the cannulation board 12 and the upper portion 28 of the fixation member 22, whereby providing a means for removably securing a relatively fixed relationship therebetween to restrict any movement of the hand 50, wrist 52 and forearm 54 during cannulation of a catheter and/or arterial blood sampling.

As further illustrated in FIGS. 1 and 2, a slight incline 32 may be formed in the elongated surface of the upper portion 28 of the fixation member 22 to provide for an expansion of the internal periphery of the cavity 30 generally at the opening disposed opposite the third angular bend 24. Preferably, the incline 32 formed in the upper portion 28 of the fixation member 22 provides for an increase in the internal periphery of the opening of the cavity 30 in order to sufficiently accommodate for the introduction and retention of the fleshy portion of the thumb and palmer region of the hand 50 of the patient. In one presently preferred embodiment of the present invention, the incline 32 formed in the upper portion 28 of the fixation member 22 comprises a sloped incline of between approximately 5° and 20°, and preferably about 10°.

Extending from the incline 32 in the upper portion 28 of the fixation member 22 is a fourth angular bend 34. The longitudinal section of the upper portion 28 of the fixation member 22 disposed between the third angular bend 24 and the fourth angular bend 34 preferably provides a linear length sufficient in dimension to secure the fingers and a substantial portion of the palmer region of the hand 50 of the patient operably disposed in relation therewith. In one presently preferred embodiment of the present invention, the length between the third angular bend 24 and the fourth angular bend 34 is between approximately 7 cm and 10 cm, and preferably about 8.5 cm. Moreover, the fourth angular bend 34 comprises an angular bend of between approximately 75° and 100°, and preferably about 85°.

Preferably disposed at the second end 16 of the cannulation board 12 is at least one retaining member 36 providing a means for retaining a cannula 62 and its attached arterial tubing 60, as illustrated in FIG. 2. In preferred structure, the retaining member 36 is formed having a substantially elongate configuration similar to that of a notch or cutout and comprising a cross-sectional area sufficient for introducing and retaining the cannula 62 in frictional engagement therewith. It will be readily appreciated, however, that other shapes or configurations of the retaining member 36 are possible.

Referring now to FIG. 3, an alternate preferred embodiment of the present invention is illustrated, as generally designated at 110, comprising at least one hinge connection 42 operably disposed adjacent the second angular bend 120 of the cannulation board 112. If desired, a second hinge connection 40 may be provided between the first end 114 and the first angular bend 118. Pursuant to the foregoing hingeable arrangement, the hinge connections 40, 42 of the wrist extending board 110 provide means for pivoting a first portion of the cannulation board 112 back on a second portion, thus making the cannulation board 112 readily compact for portability. It will be apparent to those skilled in the art that other hingeable connections or mechanisms may be constructed in accordance with the inventive principles set forth herein. It is intended, therefore, that the example provided herein be viewed as exemplary of the principles of the present invention and applicable to any one of the various preferred embodiments, and not as restrictive to a particular structure for implementing those principles.

Figure 4:
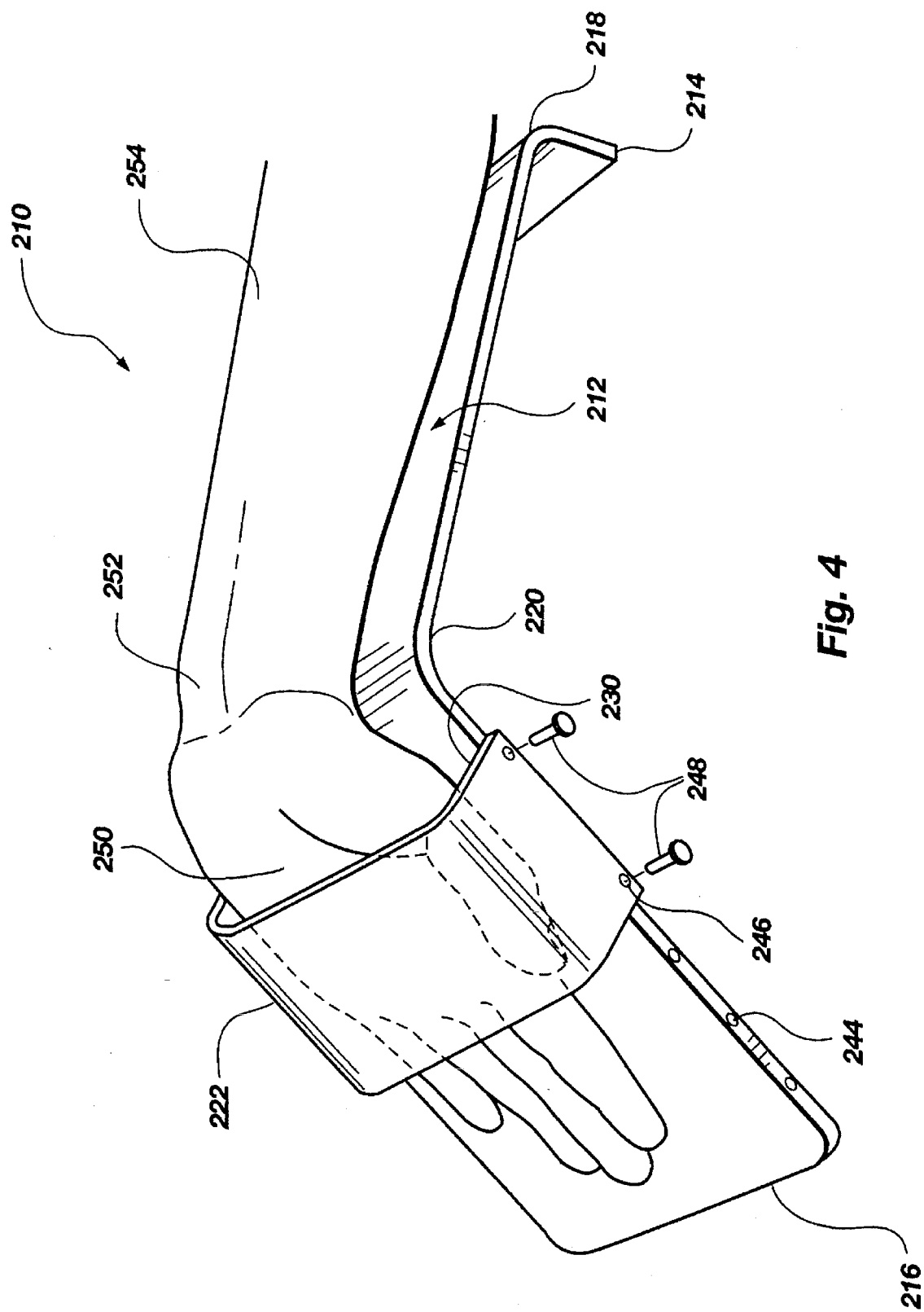
FIG. 4 is a perspective view of an alternate preferred embodiment of the wrist extending board illustrating an alternate preferred embodiment for immobilization of a patient's hand according to the present invention.

As illustrated in FIGS. 1, 2 and 3, one presently preferred embodiment of the wrist extending board 10, 110 of the present invention comprises a cannulation board 12, 112 and a fixation member 22, 122 preferably formed as a single, rigid unit. In an alternate preferred embodiment of the wrist extending board 210 of the present invention, as shown in FIG. 4, the cannulation board 212 and the fixation member 222 are independent members which interact with each other to provide means for hyperflexing the wrist 252 of a patient while providing a novel means for removably securing a relatively fixed relationship to restrict movement of the hand 250, wrist 252 and forearm 254 during cannulation of a catheter and/or arterial bloods sampling.

The alternate preferred embodiment of the wrist extending board 210 is preferably formed having a cannulation board 212 configured to include a first end 214, a first angular bend 218, a second angular bend 220 and a second end 216 having substantially the same corresponding longitudinal dimensions (length and width) and respective angular bends, as disclosed above. However, the structural relationship of the cannulation board 212 and the fixation member 222 are independently related by a fastening assembly. In this regard, the wrist extending board 210 facilitates a means for adjusting the placement of the fixation member 222 in relation to the second angular bend 220 of the cannulation board 212 to adequately insure a relatively fixed relationship between the fingers and hand 250 of a patient.

Integrally formed in the opposing longitudinal sides of the cannulation board 212 is a plurality of through-bores 244 being preferably disposed in spaced apart relation to each other. As illustrated in FIG. 4, the through-bores 244 disposed in the cannulation board 212 are preferably formed between the second angular bend 220 and the second end 216 thereof. In addition, the through-bores 244 are formed having an internal diameter sufficient in dimension to allow an elongated fastening member 248 to be rotatably introduced therein.

In similar design, integrally formed within the opposing peripheral sides of the fixation member 222 is at least one opening 246. Preferably, at least two openings 246 are formed in the peripheral sides of the fixation member 222 and readily disposed in spaced apart relation to each other. The openings 246 in the fixation member 222 are preferably formed having an internal diameter sufficient to allow for the introduction of the elongated fastening member 248 therethrough.

In preferred operation, the openings 246 formed in the fixation member 222 are disposed in alignment with the correspondingly through-bores 244 formed in the cannulation board 212, whereby an elongated fastening member 248 may be rotatably introduced through the opening 246 in the fixation member 222 and further through the corresponding through-bore 244 in the cannulation member 212 to provide a secured engagement therebetween. It will be apparent to those skilled in the art that other fastening assemblies may be provided in accordance with the inventive principles set forth herein. It is intended, therefore, that the example provided herein be viewed as exemplary of the principles of the present invention and applicable to any one of the various preferred embodiments, and not as restrictive to a particular structure for implementing those principles. Moreover, the alternate preferred embodiment shown in FIG. 4 may be formed as a single unit, wherein the fixation member 222 is rigidly secured in relation to the cannulation board 212. This variation in the configuration of the wrist extending board 210 of the present invention is readily consistent and contemplated within the spirit and scope of the present invention.

Although the present invention is illustrated and described in connection with a generally rectangular cannulation board, those skilled in the art will recognize that various other geometrical configurations are likewise suitable. The use of a generally rectangular configuration is thus by way of illustration only and not by way of restriction or limitation.

As noted above, because the hand, wrist and forearm need to be deliberately supinated from the neutral position to expose the volar aspect of the wrist for penetration by means of a needle in the radial artery, a serious disadvantage with prior art cannulation boards is their inherent inability to prevent pronation of the hand, wrist and forearm into the neutral position as a result of the natural rotational forces acting thereagainst. In this regard, the forces encouraging the pronation of the hand, wrist and forearm into the neutral position will usually rotate the attached prior art cannulation board in like manner. Accordingly, the preferred embodiments of the longitudinal surface of the cannulation board comprise a wider base sufficient to effectively prevent rotation of the hand, wrist and forearm and, in turn, the device itself.

As will be appreciated, since the wrist extending board of the present invention must generally conform to the hand, wrist and forearm of the patient to which it is to be applied, it is anticipated that various sizes, dimensions and angular bends for hyperflexing the volar aspect of the wrist of the patient will generally be desirable to accommodate the physical dimensions of the different users. In this regard, the illustrative embodiments as disclosed in detail above might be considered as an intermediate adult size from which variations may be made in order to accommodate the physical dimensions of smaller or larger adults and children.

Although numerous variations or techniques are available, one presently preferred protocol or method of using the wrist extending board of the present invention for cannulation of a catheter and/or arterial blood sampling may comprise the steps of: (1) obtaining a wrist extending board of the present invention; (2) rotating the hand, wrist and forearm of a patient in a supinated position; (3) disposing the hand, wrist and forearm in relation to the contoured wrist extending board and hyperflexing the wrist in order to expose the volar aspect thereof; (4) introducing the fingers (including the thumb) and a substantial portion of the palmer region of the hand within a cavity formed between the upper portion of the fixation member and the lower portion of the longitudinal surface of the cannulation board; (4) disposing an arterial cannula in relation to the retaining member preferably formed at the second end of the cannulation board; (5) preparing a catheter needle for cannulation and/or arterial blood sampling in the radial artery; (6) palpating the pulses of the radial artery and inserting the catheter needle therein; (7) connecting the cannula and tubing to the catheter; and (8) removing the supinated hand, wrist and forearm of the patient from its relatively fixed engagement with the wrist extending board. In operation, the wrist extending board of the present invention is not intended to restrain the hand, wrist and forearm of the patient for an extended period of time. In this regard, the present invention preferably provides means for easily removing the hand, wrist and forearm of the patient from its engagement with the wrist extending board, since an extended exposure of the wrist in a hyerflexed position may cause meaningful damage to the radial nerves.

After the performing the foregoing procedure, the hand, wrist and forearm are generally cleaned and dried. In addition, a suitable antiseptic may be sprayed over the wrist, the exposed catheter and a few inches of the connector tubing.

As will be readily appreciated by those skilled in the art, other possible modifications and adaptations to the presently preferred method using the wrist extending board of the present invention for cannulating a catheter and/or arterial blood sampling are possible which are consistent with the spirit and scope of the present invention.

Consistent with the foregoing, to prevent disconnection of the tubing from the catheter hub or dislodging the catheter from the arterial artery, a piece of tape may be placed along the course of the tubing, looped loosely around the thumb, and tapped to the wrist and forearm. Moreover, to prevent or decrease infection, an antibiotic ointment may be used at the puncture site and covered with a sterile dressing, if desired.

Cannulation of the ulnar artery is also possible using the present invention and methods of cannulation and/or arterial blood sampling. However, the radial artery will be considered as the primary cannulation site for purposes of the disclosure of at least one preferred embodiment of the present invention and method for using same.

From the above discussion, it will be appreciated that the present invention provides a novel wrist extending board having a contour shape providing an angle of extension sufficient for hyperflexing the wrist of a patient to adequately expose the volar aspect of the wrist for cannulation of a catheter and/or arterial blood sampling. Unlike prior art devices, the wrist extending board of the present invention comprises a novel fixation member providing means for securing the hand of the patient in a supinated position, without the need for multiple working components, while further preventing pronation of the hand, wrist and forearm into its neutral position in relation to the natural rotational forces acting thereagainst.

Additionally, the wrist extending board of the present invention provides a means for easily mounting or dismounting the hand, wrist and forearm of a patient from the board and which is capable of being readily cleaned and sterilized for immediate reuse by another patient. The present invention further provides a wrist extending board which provides a means for mounting the arterial tubing for easy availability in relation to reducing blood loss after cannulation. Moreover, the wrist extending board of the present invention may comprise one or more hingeable connections for making the board compact for easy portability and may further be adapted for pre-sterilization and for packaging as a disposable product, thus being generally cost effective in light of mass production and readily available for emergency procedures.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A wrist extending board for cannulation of a catheter and/or arterial blood sampling, the wrist extending board comprising:

a cannulation board having a first end, a second end and at least one angular bend disposed between said first end and said second end, said cannulation board including a longitudinal surface adapted to receive a supinated hand, wrist and forearm of a user;

said angular bend formed in said cannulation board providing means for hyperflexing the supinated wrist of the user;

a fixation member formed approximate the second end of said cannulation board, said cannulation board and said fixation member being formed of a rigid material having a substantially uniform thickness, the fixation member comprising an opening having an internal periphery being sufficient in dimension for introducing a portion of said supinated hand of said user; and said fixation member providing means for removably restricting said hand, wrist and forearm of the user in said supinated position for cannulating said catheter and sampling said arterial blood.

2. A wrist extending board as defined in claim 1 wherein said longitudinal surface of said cannulation board comprises a width sufficient to prevent pronation of said supinated hand, wrist and forearm of said user.

3. A wrist extending board as defined in claim 1 wherein said longitudinal surface of said cannulation board comprises a smooth surface.

4. A wrist extending board as defined in claim 1 wherein said longitudinal surface of said cannulation board comprises a removable covering.

5. A wrist extending board as defined in claim 1 wherein said longitudinal surface of said cannulation board comprises a substantially consistent incline extending between said first end to said angular bend.

6. A wrist extending board as defined in claim 5 wherein said longitudinal surface extending between said first end to said angular bend comprises a length sufficient to adequately support said forearm of said user.

7. A wrist extending board as defined in claim 1 further comprises a second angular bend extending from said first end.

8. A wrist extending board as defined in claim 7 wherein said second angular bend comprises an angular bend of about 40°.

9. A wrist extending board as defined in claim 1 wherein said angular bend comprises an angular bend between approximately 115° and 125°.

10. A wrist extending board as defined in claim 1 wherein said angular bend comprises a preferred angle of extension of about 120°.

11. A wrist extending board as defined in claim 1 wherein said longitudinal surface of said cannulation board comprises a substantially consistent declining slope extending from said angular bend to a third angular bend formed in the cannulation board.

12. A wrist extending board as defined in claim 11 wherein said third angular bend comprises a substantially semi-circular configuration.

13. A wrist extending board as defined in claim 1 wherein said fixation member comprising an upper portion disposed in a spaced apart relation to said longitudinal surface to form said opening.

14. A wrist extending board as defined in claim 1 wherein said cannulation board and said fixation member are formed as a single unit.

15. A wrist extending board as defined in claim 1 further comprising a retaining member disposed at said second end of said cannulation board for engageably retaining an arterial cannula.

16. A wrist extending board as defined in claim 1 further comprising at least one hinge connection disposed adjacent said angular bend of the cannulation board.

17. A wrist extending board for cannulation of a catheter and/or arterial blood sampling, the wrist extending board comprising:

a cannulation board having a first end, a second end and at least one angular bend disposed between said first end and said second end, said cannulation board including a longitudinal surface adapted to receive a supinated hand, wrist and forearm of a user, said longitudinal surface comprising a width sufficient to prevent pronation of said supinated hand, wrist and forearm of said user;

said angular bend formed in said cannulation board comprising means for hyperflexing the supinated wrist of said user, the angular bend comprising an angle of extension between approximately 115° and 125°;

a fixation member formed approximate the second end of said cannulation board, said cannulation board and said fixation member comprising a single unit being formed of a rigid material and having a substantially uniform thickness, the fixation member comprising an opening having an internal periphery being sufficient in dimension for introducing a substantial portion of the supinated hand of said user; and said fixation member providing means for removably restricting said hand, wrist and forearm of the user in said supinated position for cannulating said catheter and sampling said arterial blood.

18. A wrist extending board as defined in claim 17 further comprising at least one hinge connection disposed adjacent said angular bend of the cannulation board.

19. A wrist extending board as defined in claim 17 wherein said fixation member engages said cannulation board by means of a fastening assembly.

20. A method for cannulation of a catheter and/or arterial blood sampling, the method comprising the steps of:

rotating a hand, wrist and forearm of a user in a supinated position;

obtaining a wrist extending board of the present invention, said wrist extending board comprising a cannulation board and a fixation member, said cannulation board having a first end, a second end and an angular bend disposed between said first end and said second end;

disposing said hand, wrist and forearm of the user in relation to said wrist extending board;

positioning said wrist over said angular bend formed in the cannulation board, said angular bend providing means for hyperflexing the wrist;

introducing each finger and a substantial portion of a palmer region of said hand within an opening disposed between said fixation member and said cannulation board;

inserting a catheter needle in said radial artery;

connecting a cannula and tubing to said catheter; and removing said supinated hand, wrist and forearm of said user from its relatively fixed engagement with said wrist extending board.

\* \* \* \* \*